United States Patent [19]

Tsuji

[11] Patent Number: 4,586,190
[45] Date of Patent: Apr. 29, 1986

[54] BLOOD CELL DISCRIMINATOR AND COUNTER UTILIZING TRANSMITTED AND SCATTERED LIGHT

[75] Inventor: Fumio Tsuji, Kyoto, Japan

[73] Assignee: Shimadzu Corporation, Kyoto, Japan

[21] Appl. No.: 551,609

[22] Filed: Nov. 14, 1983

[30] Foreign Application Priority Data

Nov. 19, 1982 [JP] Japan .................. 57-203980

[51] Int. Cl.⁴ .................................... G01N 21/47
[52] U.S. Cl. ............................. 377/10; 356/39
[58] Field of Search ............ 377/10; 356/73, 72, 356/39

[56] References Cited

U.S. PATENT DOCUMENTS

| 2,875,666 | 3/1959 | Parker et al. | 356/73 |
| 3,827,805 | 8/1974 | Mansfield et al. | 356/73 |
| 4,027,973 | 6/1977 | Kaye | 356/73 |

FOREIGN PATENT DOCUMENTS

| 9307 | 4/1980 | European Pat. Off. | 356/338 |
| 131542 | 8/1983 | Japan | 356/39 |

Primary Examiner—John S. Heyman
Assistant Examiner—Karl Ohralik
Attorney, Agent, or Firm—Stiefel, Gross, Kurland & Pavane

[57] ABSTRACT

A blood counter comprising a sheathed flow cell; a light source including what has the wavelengths causing absorption of light by hemoglobin in the blood; means for receiving transmitted light; means for receiving the scattered light; a decision assembly for judging, based on the output signals detected by means for receiving the transmitted light and scattered light, (i) the flowing cells therein to be a red blood cell if the degree of absorption is larger than the preselected level and (ii) the other to be a blood platelet if the intensity of the scattered light is larger than a certain level and if the degree of absorption is smaller than said preselected level; and a counter assembly for counting out the red blood cells and blood platelets.

6 Claims, 3 Drawing Figures

BLOOD CELL DISCRIMINATOR AND COUNTER UTILIZING TRANSMITTED AND SCATTERED LIGHT

BACKGROUND OF THE INVENTION

1. Field of the Invention

The present invention relates to a blood counter, and more particularly to an apparatus for counting blood cells by distinguishing between erythrocytes (red blood cells are abbreviated as RBCs) and thrombocytes(blood platelets are abbreviated as PLTs) readily and correctly.

2. Description of the Prior Art

Heretofore, use has been made of an automatic blood counter wherein the cells of blood are irradiated with laser beams while they are made to pass successively to cause the light to scatter, and the scattering intensity and the transit time are used to distinguish between blood cells (the Japanese Patent Laying-open No. 30694/1980). In addition, an apparatus using the electric resistance method (the so-called COULTER method) is also in use.

Although the detection of leukocytes (white blood cells are abbreviated as WBCs) in the conventional apparatus poses no problem because they are detected independently of RBCs and PLTs by adding a hemolytic agent and the like to destroy the latter, the disadvantage is that RBCs and large PLTs, both of which are almost the same in size, cannot be distinguished with sufficient accuracy.

It has accordingly been proposed to mathematically process them for distinguishing purposes; however, the problem is that it tends to make the arrangement too complicated.

There has not yet been proposed a blood counter utilizing absorption of light by hemoglobin in the RBC.

SUMMARY OF THE INVENTION

The present invention has made it possible to accurately count blood cells by detecting the light scattered by blood cells and absorption of light by hemoglobin.

An object of the present invention is to provide a blood counter comprising a sheathed flow cell in which each particle of the cells of blood is flowed separately and successively; a light source for radiating light on the sheathed flow cell, the light including what has the wavelengths causing absorption of light by hemoglobin in the blood; means for receiving transmitted light to detect the degree of absorption by hemoglobin from the light transmitted across the sheathed flow cell; means for receiving the scattered light to detect the intensity of the light scattered from the sheathed flow cell; a decision assembly for judging, based on the output signals detected by the means for receiving the transmitted light and scattered light, (i) the flowing cell therein to be a RBC if the degree of absorption is larger than the preselected level and (ii) the other to be a PLT if the intensity of the scattered light is larger than a certain level and if the degree of absorption is smaller than the preselected level; and a counter assembly for counting out the RBCs and PLTs.

Another object of the present invention is to provide the method of accurately distinguishing between RBCs and PLTs according to the intensity of the scattering and absorption of light by irradiating the cells in blood with light including what has the wavelengths (for instance, about 415 nm or 540 nm) having the light readily absorbed into hemoglobin.

By the light including what has the wavelengths having the light readily absorbed into hemoglobin is meant such light including what has both the wavelengths having the light readily and hardly absorbed into hemoglobin; the former and the latter are used to detect the degrees of absorption and scattering, respectively.

DESCRIPTION OF THE PREFERRED EMBODIMENT

Figure 1:
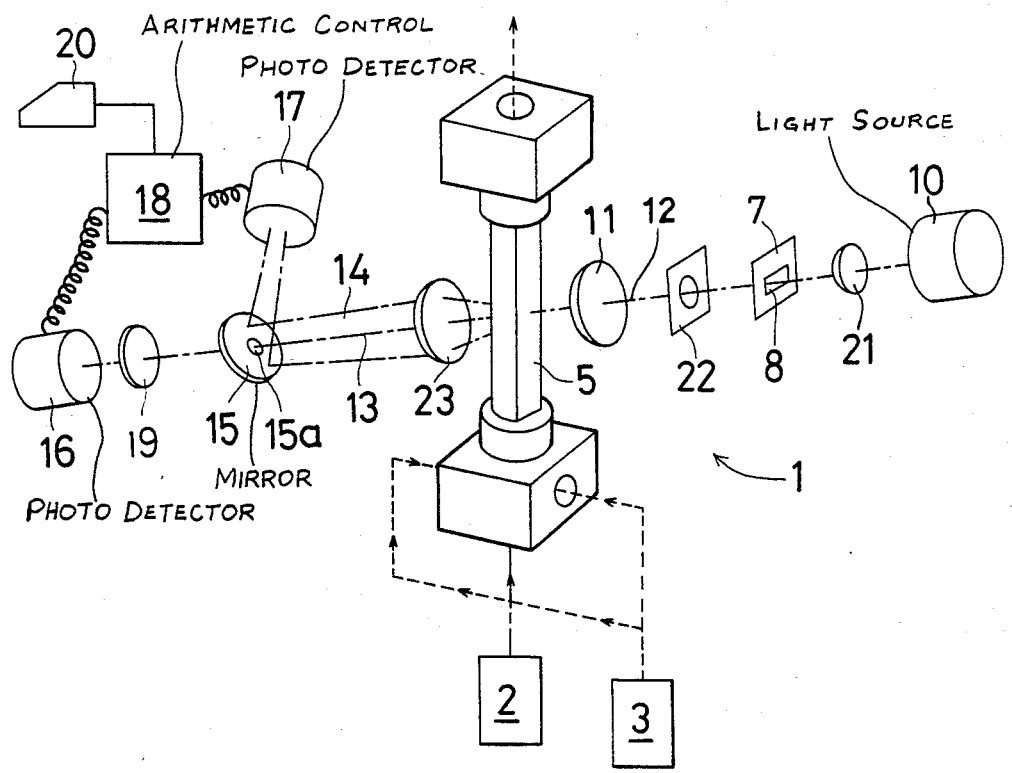
FIG. 1 is an illustration of an embodiment of the blood counter in accordance with the present invention.
Figure 2:
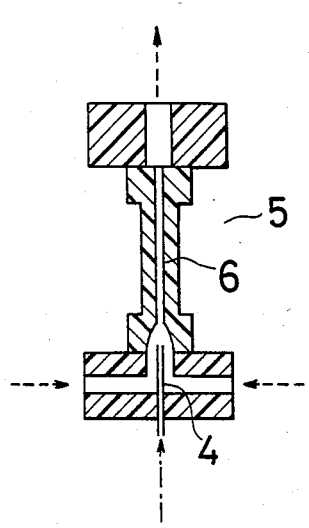
FIG. 2 is a section of the flow cell shown in FIG. 1.

Numeral 1 in the drawing indicates a blood counter used to distinguish between RBCs and PLTs contained in a blood specimen and to count them.

The blood specimen is diluted with a physiological salt solution and discharged from a specimen discharge tube 4 by a pump 2 for the specimen. The specimen discharge tube 4 is contained in a sheathed flow cell 5 and a laminar flow of the physiological salt solution sent from a pump 3 for a sheath flow is formed. Consequently the blood specimen flow is changed into a sheathed flow with a fine diameter. The diameter of a flow passage 6 being examined is about 200 $\mu$m and becomes the sheath flow diameter, whereas the diameter of the specimen flow within the sheath flow is about 20 micrometer($\mu$m) Since the blood has been diluted and reduced to a fine sheathed flow, the cells therein are made to flow successively with spacings in the flow passage 6 being examined. The sheathed specimen flow discharged from the flow passage 6 being examined is not used.

The sheathed specimen flow in the flow passage 6 being examined is irradiated with measuring light 12 having wavelengths including the maximum wavelength (about 415 nanometer(nm) absorbable by hemoglobin in the form of a beam by a light source 10 such as an Xe lamp or halogen lamp, whereby an image of a slit 8 is projected by a lens 11. Numerals 21 and 22 are a condensing lens and a diaphragm, respectively.

The light passed through the sheathed specimen flow is divided into transmitted light 13 and scattered light 14. The transmitted light 13 is incident on the center of a light receiving lens 23, whereas the scattered light 14 is incident on the periphery thereof.

The transmitted light 13 that has made an exit through the center of the light receiving lens 23 passes through a central hole 15a of a doughnut mirror 15 and then an interference filter 19 allowing the maximum wavelength (about 415 nm) absorbable by the hemoglobin to pass therethrough. The transmitted light 13 is detected by a photodetector such as a photomultiplier tube, whereas the scattered light 14 is reflected by the mirror 15, before being detected by a photodetector 17 as in the case of 16.

Figure 3:
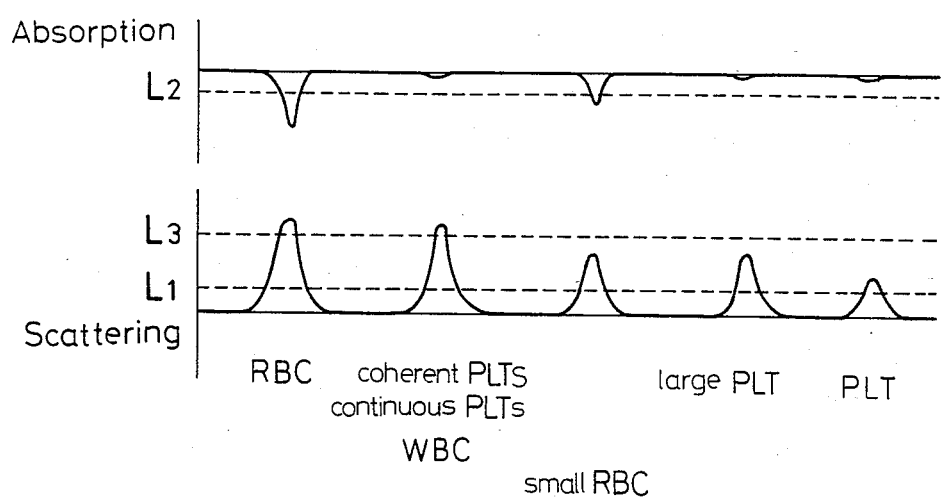
FIG. 3 is a chart explanatory of signals in the counter shown in FIG. 1.

Numeral 18 is an arithmetic control such as a microcomputer, which is used to recognize the intensity of the absorbed light based on the signal applied by the photodetector 16. Moreover, the arithmetic control also recognizes the intensity of the scattered light based on the signal applied by the photodetector 17. As shown in FIG. 3, if the intensity of the scattered light becomes larger than the preselected level (L1), the arithmetic control will determine the presence of a cell and checks the intensity of the absorbed light: if the intensity of the absorbed light is larger than the preselected level (L2), it will determine the cell to be a RBC and include in the count. On the other hand, if the intensity of the absorbed light is smaller than the preselected level (L2), it will determine the cell to be a PLT. However, it again checks the intensity of the scattered light and counts only those with the scattered light at less than the preselected level (L3) as platelets and those with the scattered light at more than (L3) as "others". This is because it is preferred that those showing almost no absorption of light and the great intensity of the scattered light should not be counted as PLTs statistically, as such phenomena are observed in case they are coherent with each other or they are continuously passed as if interlockingly, or they are WBCs.

As noted above, the present invention makes it possible to accurately distinguish between RBCs and PLTs and count them without using none of dyeing agents, fluorescent reagents, hemolytic agents and so on. This enable the discrimination to be made much easier and quicker than the case of mathematical processing.

As many apparently widely different embodiments of this invention may be made without departing from the spirit and scope thereof, it is to be understood that the invention is not limited to the specific embodiments thereof except as defined in the appended claims.

I claim:

1. A blood counter comprising a sheathed flow cell in which each particle of the cells of blood is flowed separately and succesively; a light source for radiating light on said sheathed flow cell, the light including light having the wavelengths for causing absorption of light by hemoglobin in the blood; a portion of said light being transmitted across said sheathed flow cell; a portion of said light being scattered from the sheathed flow cell, means for receiving transmitted light to detect the degree of absorption by hemoglobin from the light transmitted across said sheathed flow cell; means for receiving the scattered light to detect the intensity of the light scattered from the sheathed flow cell; a decision assembly for judging, based on the output signals detected by means for receiving the transmitted light and scattered light, (1) the flowing cells therein to be a red blood cell if the degree of absorption is larger than the preselected level and (11) the other material to be a blood platelet if the intensity of the scattered light is larger than a certain level and if the degree of absorption is smaller than said preselected level; and a counter assembly for counting out the red blood cells and blood platelets.

2. A blood counter as claimed in claim 1, wherein said light source radiates light including what has a wavelength of 415 nm as the light causing hemoglobin in blood to absorb it.

3. A blood counter as claimed in claim 1, wherein said light source is a white one.

4. A blood counter as claimed in claim 1, wherein said means for receiving the transmitted light comprises an interference filter and a photomultiplier tube.

5. A blood counter as claimed in claim 1, wherein said means for receiving the scattered light comprises a doughnut mirror and a photomultiplier tube receiving the scattered light reflected by said mirror.

6. A blood counter as claimed in claim 1, wherein said decision and counter assemblies comprise a microcomputer system.

* * * * *